United States Patent [19]

Ishiguro et al.

[11] Patent Number: 4,629,600
[45] Date of Patent: Dec. 16, 1986

[54] METHOD AND APPARATUS FOR MEASURING URANIUM ISOTOPE ENRICHMENT

[75] Inventors: Nobuharu Ishiguro, Yokohama; Akira Kurosawa, Hitachi, both of Japan

[73] Assignee: Doryokuro Kakunenryo Kaihatsu Jigyodan, Tokyo, Japan

[21] Appl. No.: 590,915

[22] Filed: Mar. 15, 1984

[30] Foreign Application Priority Data

Apr. 13, 1983 [JP] Japan .................. 58-64750

[51] Int. Cl.$^4$ .......................................... G21C 17/06
[52] U.S. Cl. ..................................... 376/257; 376/157
[58] Field of Search ...................... 376/157, 153, 257

[56] References Cited

U.S. PATENT DOCUMENTS

| 4,031,388 | 6/1977 | Morita et al. | 376/157 |
| 4,229,654 | 10/1980 | Arya et al. | 376/257 |
| 4,497,768 | 2/1985 | Caldwell et al. | 376/257 |

FOREIGN PATENT DOCUMENTS

| 2621358 | 11/1977 | Fed. Rep. of Germany | 376/257 |
| 54-140094 | 10/1979 | Japan | 376/257 |
| 57-151881 | 9/1982 | Japan . | |

Primary Examiner—Salvatore Cangialosi
Attorney, Agent, or Firm—Wenderoth, Lind & Ponack

[57] ABSTRACT

A method and apparatus for measuring uranium isotope enrichment in a sample uranium solution. In the invention, the concentration of uranium in the uranium solution is determined by K-edge densitometry. The quantity of uranium-235 in the uranium solution is then measured by detecting the gamma rays emitted from the uranium-235 by using a high-purity germanium detector. A value of the uranium isotope enrichment is obtained from the ratio of the quantity of uranium-235 in the uranium solution to the uranium concentration. The invention is designed to provide the improved construction of a radiation source suitable for the K-edge densitometry and to provide the accurate measurements by correcting any error in the measured quantity of uranium-235 in the uranium solution due to the self-absorption of the gamma rays emitted from the uranium-235.

8 Claims, 4 Drawing Figures

METHOD AND APPARATUS FOR MEASURING URANIUM ISOTOPE ENRICHMENT

BACKGROUND OF THE INVENTION

The present invention relates in general to a method and apparatus for measuring uranium isotope enrichment (the uranium-235 content) in a uranium solution, and more particularly, although not limited, to a method and apparatus in which uranium isotope enrichment in processing steps is detected and supervised to provide criticality safety control, for example, in a uranium denitration system in spent nuclear fuel reprocessing facilities.

It is usualy important in uranium denitration system that the uranium isotope enrichment is supervised so that it stays at a constant value, or below it, thereby preventing the threat of a critical state arising. This supervision of the uranium isotope enrichment must be carried out quickly in view of the process of the system.

A mass spectrograph which is large in size and difficult to maintain is used conventionally for measuring the uranium isotope enrichment of a uranium solution, therefore it is inevitably necessary to provide pretreatment for applying a sample to be measured onto a special filament, a long measurement time, and the operation of special apparatus. The uranium isotope enrichment thus cannot be measured quickly and simply.

There is also a passive assay method of measuring uranium isotope enrichment which uses an X-ray tube or special radiation (ytterbium-169). However, in the method using the X-ray tube, a special, large high-voltage power unit is required for the X-ray tube, and also large quantities of unnecessary X-rays are produced by the X-ray tube so that a special energy filter is needed through which the required X-rays only are selectively extracted, and also a large shield is necessary. With the latter method using special radiation, a sealed active source is required, and the decay of the working source is quick (the half-life of ytterbium-169 is 32 days) and thus the apparatus cannot be maintained normally unless the radiation source is replaced about five times a year.

Such being the circumstances, neither method is applicable for the purpose of rapidly supervising the uranium isotope enrichment of a uranium solution particularly in the uranium denitration system described above.

Recently, however a method for solving these defects has been proposed (Japanese Patent Application Laid-Open No. 57-151881, laid-open Sept. 20, 1982), which comprises irradiating photons of an energy lower than the uranium K-edge energy and other photons of an energy higher than that energy onto a sample containing uranium to determine the concentration of uranium in the sample from the respective intensities of the photons which penetrate the sample, measuring an intensity of gamma rays emitted from the sample due to the alpha decay of uranium-235 in the sample, and obtaining a value of uranium isotope enrichment from the measured intensity of gamma rays and the concentration of uranium. An apparatus for practising the above-described method has also be proposed, which comprises a radiation source emitting photons of an energy lower than the uranium K-edge energy and other photons of an energy higher than that energy, a shutter capable of selectively shutting off the photons from the radiation source, a sample onto which the photons are irradiated through the shutter and through a collimator, a photon detector for detecting the intensity of the photons which penetrate the sample and the intensity of gamma rays emitted from the sample due to the alpha decay of uranium-235 in the sample, and a measuring electronic system including a pulse height analyzer for processing outputs of the photon detector.

This method and apparatus are advantageous for measuring uranium isotope enrichment quickly and easily, and is particularly effective for the purpose described above. However, no disclosure is made of a concrete example of the radiation source, and there are still problems remaining such that an apparatus which is compact and easy to maintain cannot be constructed from conventional prior art techniques, and that the measurement accuracy cannot be improved because of errors arising from the self-absorption of gamma rays emitted from uranium-235 in the sample.

SUMMARY OF THE INVENTION

An object of the present invention is to provide an improved method for measuring uranium isotope enrichment.

Another object of the present invention is to provide an improved method for measuring uranium isotope enrichment, which permits a simple, accurate and quick measurement without requirement of particular skills in operation for the pretreatment of a sample.

Another object of the present invention is to provide an improved method for measuring uranium isotope enrichment, which permits a complete miniaturization of an apparatus therefor.

Additional object of the present invention is to provide an improved method for measuring uranium isotope enrichment, which permits continuous, automatic measurements.

A further object of the present invention is to provide a new apparatus for measuring uranium isotope enrichment, which permits a simple, accurate and quick measurement without requirement of particular skills.

Another object of the present invention is to provide an improved apparatus for measuring uranium isotope enrichment, which can be simple and small-sized.

Another object of the present invention is to provide a new apparatus as described, which permits continuous, automatic measurements.

In principle, the present invention provides a method and apparatus for measuring uranium isotope enrichment, in which the concentration of uranium in a sample uranium solution is determined by K-edge densitometry, and the quantity of uranium-235 in the uranium solution is measured by detecting gamma rays (passive gamma rays: 186 KeV) that uranium-235 itself emits by using a high-purity germanium detector. A value of the uranium isotope enrichment is then obtained from the ratio of the quantity of uranium-235 in the uranium solution to the uranium concentration. The present invention is designed to provide the improved construction of a radiation source suitable for the K-edge densitometry and to provide the accurate measurements by correcting any error in the measured quantity of uranium-235 in the uranium solution due to the self-absorption of the gamma rays emitted from the uranium-235.

Briefly, the present invention provides an improvement in a method for measuring uranium isotope enrichment including the steps of irradiating photons of an energy lower than the uranium K-edge energy and other photons of an energy higher than that energy onto a sample containing uranium to determine the concentration of uranium in the sample from the respective intensities of the photons which penetrate the sample, measuring an intensity of gamma rays emitted from the sample due to the alpha decay of uranium-235 in the sample, and obtaining a value of uranium isotope enrichment from the measured intensity of gamma rays emitted from the uranium-235 in the sample and the concentration of uranium in the sample. The improvement according to the method of the present invention is that the photons irradiated onto the sample are produced by an interaction of a sealed radiation source of cobalt-57 with an uranium foil, and that a piece of highly-enriched uranium metal is disposed in the vicinity of the sample so as to separately measure intensities of gamma rays emitted from the highly-enriched uranium metal at the time of no sample present and at the time of the sample being present. Thus, a self-absorption correction factor of gamma rays in the sample is obtained from the function of the intensity of gamma rays at the time of no sample present and of the intensity of gamma rays at the time of the sample being present, thereby correcting the measured intensity of gamma rays emitted from the uranium-235 in the sample.

The present invention also provides an improvement in an apparatus for measuring uranium isotope enrichment including a radiation source emitting photons of an energy lower than the uranium K-edge energy and other photons of an energy higher than that energy, a collimator system arranged along an optical path through which the photons emitted from the radiation source pass, a movable shutter mechanism provided across the optical path and capable of selectively shutting off the photons from the radiation source, a sample containing uranium disposed in the optical path and onto which the photons are irradiated through the shutter mechanism and the collimator system, a photon detector for detecting the intensity of the photons which penetrate the sample and the intensity of gamma rays emitted from the sample due to the alpha decay of uranium-235 in the sample, and a measuring electronic system including a pulse height analyzer for processing outputs of the photon detector. The improvement according to the apparatus of the present invention is that the radiation source comprises a sealed radiation source of cobalt-57 and a uranium foil disposed adjacent to the sealed radiation source, and that the shutter mechanism has a piece of highly-enriched uranium metal embedded therein such that gamma rays emitted from the highly-enriched uranium metal are irradiated towards the sample when the shutter mechanism shut off the photons from the radiation source.

The invention will be more clearly understood from the following detailed description of a preferred embodiment, which will be made with reference to the accompanying drawings.

DETAILED DESCRIPTION OF THE INVENTION

Figure 1:
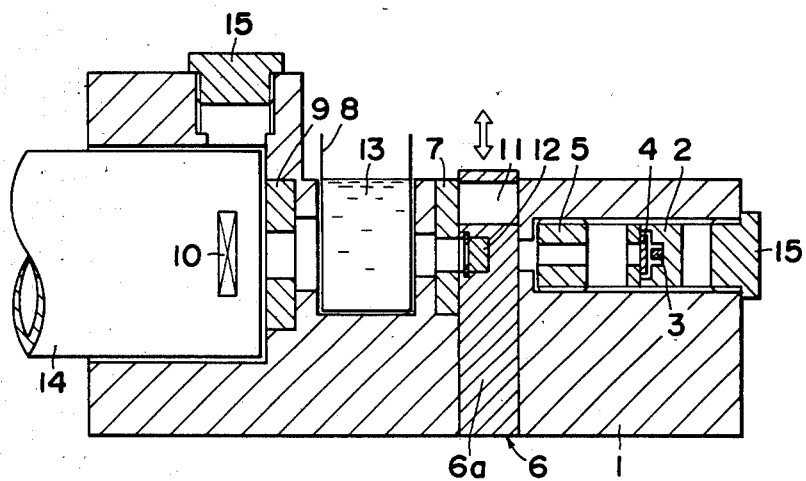
FIG. 1 is a longitudinally sectional view of a measuring apparatus embodying the present invention.
Figure 2:
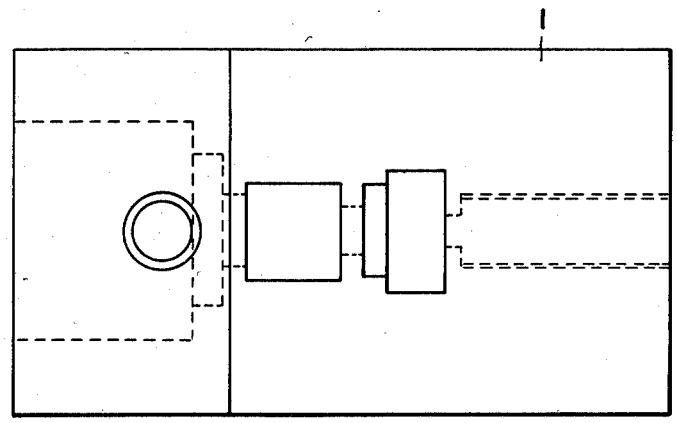
FIG. 2 is a plan view of a shield block used in the apparatus shown in FIG. 1.

With reference to FIGS. 1 and 2, elements and members of the apparatus according to the invention are mounted in their specific mounting holes provided on a lead or tungsten shield block 1. A radiation source used in the apparatus comprises a sealed radiation source 3 of cobalt-57 mounted in a radiation source holder 2 and a uranium foil 4 provided over the front thereof. Thus, in addition to two kinds of gamma rays (at 122 KeV and 136 KeV) emitted from the cobalt-57 radiation source 3, X-rays ($UK_{\alpha 1}$ X-rays at 98 KeV; $UK_{\alpha 2}$ X-rays at 94 KeV, etc.) are generated by interaction between the gamma rays and the uranium foil 4. The uranium foil 4 is preferably foil of uranium-238, but natural uranium may be used since it does not have any undesirable effect on the accuracy of measurement.

Figure 3:
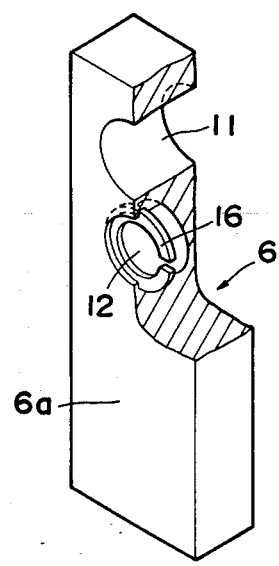
FIG. 3 is a fragmentary perspective view of a shutter used in the apparatus shown in FIG. 1.

In FIG. 1, the apparatus has a first collimator 5, a shutter 6, a second collimator 7, a sample cell 8, a third collimator 9, and a high-purity germanium detector 10, which are arranged in that order along the passage of the photons (gamma rays and X-rays) emitted from the radiation source 3. The collimators 5, 7 and 9 are made of tungsten and collimate the photons passing through them. The shutter 6 is made of tungsten and, as shown in FIG. 3, a through-hole 11 is provided on the first portion thereof, and a piece of highly-enriched uranium metal 12 is embedded in the second portion of the shutter 6 with its one surface exposed in the direction of the sample cell 8 and fixed in position by a ring 16. As indicated by an arrow in FIG. 1, the shutter 6 is slidable in the shield block 1 so as to selectively open and close the passage through which the photons from the radiation source 3 irradiates in the direction of the sample cell 8. Thus, the irradiation of the photons to the sample cell 8 is selectively controlled and also the highly-enriched uranium metal 12 is selectively placed into a facewise relation with the sample cell 8. The sample cell 8 is designed to contain therein a uranium solution 13, and removably inserted from the top of the shield block 1. In a practical application, although not illustrated, an automatic sample changer may be provided so that sample cells can be replaced automatically and continuously. The high-purity germanium detector 10 is mounted in a detector head 14 which is then inserted and held horizontally in the shield block 1. Outputs from the detector 10 are fed to and processed in a measuring electronic system (not shown) which includes a pulse height analyzer. Openings provided on the shield block 1 are closed with lead or tungsten plugs 15, as illustrated in FIG. 1.

The gamma rays and X-rays emitted from the radiation source 3 are collimated by the first collimator 5 and the second collimator 7 when the shutter 6 is open, and then pass through the uranium solution 13 in the sample cell 8, and are detected by the high-purity germanium detector 10 after passing through the third collimator 9. The gamma rays and the X-rays which arrived at the detector 10 are converted into electrical signals, which are then sorted into gamma spectra and stored by the measuring electronic system including the pulse height analyzer. Conventional apparatus known in this technical field is applicable for the system, and hence no further description will be made. Suffice it to say that the intensities of gamma rays and X-rays can be measured by this measuring electronic system.

Of these gamma rays and X-rays, those with an energy of 122 KeV and 94 KeV (or 98 KeV) are close to the K-edge energy or uranium, and the absorption ratio thereof varies according to the concentration of the uranium solution through which the gamma rays and X-rays pass. Therefore the concentration of the uranium solution can be obtained from the absorption ratio. This method is called "K-edge densitometry".

A specific method for measuring the concentration of uranium solution will be described below. Assume that the intensities of the gamma rays (122 KeV) and the X-rays (94 KeV or 98 KeV) detected by the high-purity germanium detector 10 are $I_{10}$ and $I_{20}$, respectively, when there is no uranium solution in the sample cell 8 and the shutter 6 is open. Assume also that these intensities of the gamms rays (122 KeV) and X-rays (94 KeV or 98 KeV) when there is uranium solution in the sample cell 8 are $I_{11}$ and $I_{21}$, respectively. In this case, the relationship between the concentration $\rho(g/l)$ of uranium in the uranium solution 13 in the sample cell 8 and the intensities of the gamma rays and X-rays is given by the following equation (1):

$$\rho = \frac{1}{-\Delta\mu x} \ln\left(\frac{I_{11}/I_{10}}{I_{21}/I_{20}}\right) \tag{1}$$

where $\Delta\mu x$ is an apparatus constant (proportional constant). Since this equation (1) is well known and is also given in the aforementioned Japanese Patent Application Laid-Open No. 57-151881, an explanation of the equation is omitted. The uranium concentration can be obtained from equation (1) by putting a uranium solution whose uranium concentration is unknown into the sample cell 8 and measuring the intensities ($I_{11}$, $I_{21}$) of the gamma rays and X-rays passing through the uranium solution, after determining the apparatus constant by using a uranium solution whose uranium concentration is known.

The concentration of uranium-235 in the uranium solution can be obtained by detecting the gamma rays (passive gamma rays at 186 KeV), which are emitted at a constant ratio by the uranium-235 itself contained in the uranium solution 13, directly by means of the high-purity germanium detector. The gamma ray intensity in this case is denoted by $i_s$. However, the gamma rays emitted by the uranium-235 within the uranium solution are absorbed and attenuate (self-absorption) before reaching the surface of the sample cell 8, by substances such as uranium and water present in the solution.

In the present invention, the highly-enriched uranium metal 12 is embedded in the shutter 6 in order to determined the accurate ratio of self-absorption. In this way, the self-absorption correction factor can be obtained accurately, and consequently the measurement accuracy is improved. The method for obtaining the self-absorption correction factor will be explained hereinafter.

First, gamma rays (186 KeV) from the uranium-235 in the uranium solution 13 are measured by the high-purity germanium detector 10 and the intensity ($i_s$) thereof is obtained. At the time of measurement of the intensity ($i_s$), it is preferable to shield gamma rays and X-rays from the radiation source 3 by, for example, utilizing a solid portion 6a of the shutter 6 to close the optical path of the radiation source 3. However, the intensity ($i_s$) can be measured without any problem in case that the shutter 6 is maintained open to permit photons from the radiation source 3 to irradiate towards the uranium solution 13, since an energy of gamma rays from uranium-235 in the uranium solution 13 is higher than, and distinguished from, that of photons from the radiation source and can be detected by the detector 10. In the next step, the shutter 6 is closed as illustrated in FIG. 1 so that the position of the highly-enriched uranium metal 12 in the shutter 6 is aligned with the opening of the second collimator 7 and at the same time gamma rays and X-rays from the radiation source 3 are shielded. The gamma rays (186 KeV) emitted from the highly-enriched uranium metal 12 in this position are collimated by the second collimator 7 and attenuate in the uranium solution 13, and are then detected by the detector 10 through the third collimator 9. The intensity thereof in this case is denoted by ($i_{s+m}$). On the other hand, the gamma rays (186 KeV) emitted from the highly-enriched uranium metal 12 are also detected by the detector 10 when the shutter 6 is closed and there is no uranium solution in the sample cell 8, and the intensity ($i_{mo}$) thereof is obtained. The self-absorption correction factor of the gamma rays (186 KeV) from the uranium-235 in the uranium solution can be obtained accurately from the function of the difference between two intensities ($i_{s+m} - i_s$), and of the intensity ($i_{mo}$). Namely, the self-absorption correction factor CF can be obtained theoretically as the following function of the intensities ($i_{s+m} - i_s$) and ($i_{mo}$):

$$CF = \frac{1 - \left(\frac{i_{s+m} - i_s}{i_{mo}}\right)}{-\ln\left(\frac{i_{s+m} - i_s}{i_{mo}}\right)} \tag{2}$$

Finally, the concentration y of uranium-235 contained in the uranium solution is corrected by this self-absorption correction factor CF and thus can be expressed as follows:

$$y = (K \cdot i_s)/CF \tag{3}$$

where K is an apparatus constant (proportional constant).

Accordingly, the quantity of uranium-235 can be obtained from equation (3) by putting a uranium solution containing an unknown quantity of uranium-235 into the sample cell 8 and measuring the gamma ray intensity, after determining the apparatus constant K by using uranium solution in which the quantity of uranium-235 is known.

The uranium isotope enrichment E of the uranium solution can finally be obtained by the following equation (4) from the ratio of the uranium-235 quantity y to the uranium concentration $\rho$ in the uranium solution 13 (both y and $\rho$ being obtained from equations (1) and (3), respectively:

$$E(\%) = (y/\rho) \times 100 \tag{4}$$

Operative Example

Three different uranium solutions with varying uranium concentration and uranium isotope enrichment were prepared as sample solutions, and measurements were carried out on them, using the apparatus shown in FIG. 1. The measuring electronic system used comprised an amplifier, a pulse height analyzer, an electronic computer etc. In this example, the number of measurements was twice for each sample solution and the times taken for each measurement were 50 minutes.

Accurate values were measured separately for the uranium concentrations of the sample solutions by chemical analysis and for the uranium isotope enrichment by mass spectrography. These accurate values were each compared with values measured by the present invention to obtain deviations.

The results of these measurements are given in Table 1.

TABLE 1

| Sample | Uranium conc. (Chemical analysis) (g/l) | Uranium isotope enrichment* (Mass spectrography) (wt % of U-235) | Uranium conc. (g/l) according to the invention (Deviation: %)** | Uranium isotope enrichment (wt % of U-235) according to the invention (Deviation: %)*** |
|---|---|---|---|---|
| No. 1 | 400.3 g/l | 1.269 wt % | 413.2 g/l (3.2%) | 1.403 wt % (10.6%) |
|  |  |  | 408.2 g/l (2.0%) | 1.394 wt % (9.9%) |
| No. 2 | 312.9 g/l | 1.225 wt % | 318.7 g/l (1.9%) | 1.374 wt % (12.2%) |
|  |  |  | 318.2 g/l (1.7%) | 1.196 wt % (−2.4%) |
| No. 3 | 216.7 g/l | 1.135 wt % | 207.3 g/l (−4.3%) | 1.053 wt % (−7.2%) |
|  |  |  | 207.2 g/l (−4.4%) | 0.953 wt % (−16.0%) |

*Two measured values

** $\frac{\text{(Measured value)} - \text{(Chemical analysis value)}}{\text{(Chemical analysis value)}} \times 100$

Figure 4:
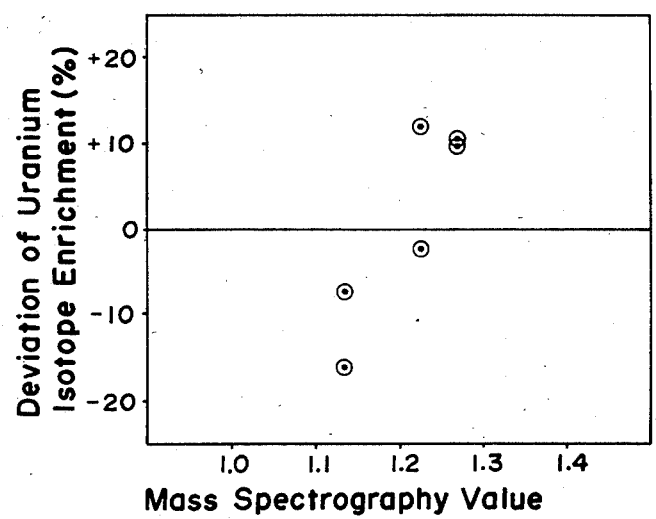
FIG. 4 is a graph showing one example of the measurement result obtained in accordance with the present invention.

*** $\frac{\text{(Measured value)} - \text{(Mass spectrography value)}}{\text{(Mass spectrography value)}} \times 100$ FIG. 4 is a graph which shows the results of the measurements in Table 1. In the graph, the uranium isotope enrichment of the samples obtained by mass spectrography is represented by and along the abscissa, and the deviation (%) between the value measured according to the method of the present invention and the value obtained by mass spectrography is represented by and along the ordinate. The deviation from the mass spectrography values was within 10% on average.

According to the present invention, the measurement time can be reduced by about 1 hour compared with the conventional mass spectrography which generally needs 5 to 6 hours, and special pretreatment operation and skills for operation of the apparatus are not required. Therefore the apparatus can be simple and free from any danger of induced errors, and moreover the effects due to the self-absorption of the uranium in the sample can be corrected to improve the measurement accuracy. Further, the apparatus can be small-sized by the use of the sealed radiation source in which cobalt-57 and uranium soil and combined, and since cobalt-57 has a long half-life (270 days), the radiation source need not be replaced so often but the frequency with which the radiation source must be replaced by new one can be reduced to about once a year. This makes it easy to control the maintenance of the apparatus and allows a continuous, automatic measurement by simply mounting an automatic sample changer in the apparatus to enhance the advantages of the present invention.

While the invention has been described with respect to a preferred embodiment, it should be apparent to those skilled in the art that numerous modifications may be made thereto without departing from the scope of the invention.

What is claimed is:

1. A method for measuring uranium isotope enrichment including the steps of irradiating photons of an energy lower than the uranium K-edge energy and other photons of an energy higher than that energy onto a sample containing uranium to determine the concentration of uranium in the sample from the respective intensities of the photons which penetrate the sample, measuring an intensity of gamma rays emitted from the sample due to the alpha decay of uranium-235 in the sample, and obtaining a value of uranium isotope enrichment from the measured intensity of gamma rays emitted from the uranium-235 in the sample and the concentration of uranium in the sample, characterized in that the photons irradiated onto the sample are produced by an interaction of a sealed radiation source of cobalt-57 with an uranium foil, and that a piece of highly-enriched uranium metal is disposed in the vicinity of the sample so as to separately measure intensities of gamma rays emitted from the highly-enriched uranium metal at the time of no sample present and at the time of the sample being present, and a self-absorption correction factor of gamma rays in the sample is obtained from the function of the intensity of gamma rays at the time of no sample present and of the intensity of gamma rays at the time of the sample being present, thereby correcting the measured intensity of gamma rays emitted from the uranium-235 in the sample.

2. An apparatus for measuring uranium isotope enrichment including a radiation source emitting photons of an energy lower than the uranium K-edge energy and other photons of an energy higher than that energy, a collimator system arranged along an optical path through which the photons emitted from the radiation source pass, a movable shutter mechanism provided across the optical path and capable of selectively shutting off the photons from the radiation source, a sample containing uranium disposed in the optical path and onto which the photons are irradiated through the shutter mechanism and the collimator system, a photon detector for detecting the intensity of the photons which penetrate the sample and the intensity of gamma rays emitted from the sample due to the alpha decay of uranium-235 in the sample, and a measuring electronic system including a pulse height analyzer for processing outputs of the photon detector, characterized in that said radiation source comprises a sealed radiation source of cobalt-57 and a uranium foil disposed adjacent to the sealed radiation source, and that said shutter mechanism has a piece of highly-enriched uranium metal such that gamma rays emitted from the highly-enriched uranium metal are irradiated towards the sample when the shutter mechanism is driven to shut off the photons from said radiation source.

3. The apparatus according to claim 2, wherein the photon detector comprises a high-purity germanium detector.

4. The apparatus according to claim 2, wherein said shutter mechanism has a through-hole at a first portion thereof, and said highly-enriched uranium metal is embedded in a second portion of the shutter mechanism with its one surface exposed in the direction of said sample, said first and second portions being selectively positioned in said optical path in accordance with the movement of said shutter mechanism.

5. The apparatus according to claim 2, wherein said uranium foil in said radiation source is a foil of uranium-235 or natural uranium.

6. The apparatus according to claim 2, wherein said collimator system has a first collimator disposed between said radiation source and said shutter mechanism, a second collimator disposed between said shutter mechanism and said sample, and a third collimator disposed between said sample and said photon detector.

7. The apparatus according to claim 2, wherein said sample is contained in a removable sample cell.

8. The apparatus according to claim 2, wherein said optical path is provided in a shield block, and said radiation source, said collimator system, said shutter mechanism, said sample and said photon detector are disposed within said shield block along said optical path.

* * * * *